United States Patent
Molinoff et al.

(10) Patent No.: US 6,312,717 B1
(45) Date of Patent: Nov. 6, 2001

(54) METHOD FOR TREATMENT OF ANXIETY AND DEPRESSION

(75) Inventors: Perry B. Molinoff, Weston; Geoffrey C. Dunbar, Middleton, both of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/333,176

(22) Filed: Jun. 14, 1999

Related U.S. Application Data
(60) Provisional application No. 60/091,993, filed on Jul. 7, 1998.

(51) Int. Cl.[7] ................................................ A61K 31/00
(52) U.S. Cl. .......................... 424/449; 424/448; 424/457
(58) Field of Search ..................................... 424/449, 448, 424/457

(56) References Cited

U.S. PATENT DOCUMENTS

| | | |
|---|---|---|
| 3,717,634 | 2/1973 | Wu et al. . |
| 4,423,049 | 12/1983 | Temple, Jr. . |
| 4,507,303 | 3/1985 | Ishizumi et al. . |
| 4,818,756 | 4/1989 | Seidel et al. . |

FOREIGN PATENT DOCUMENTS
WO 99/61014 * 2/1999 (WO) .

OTHER PUBLICATIONS

Magid Aboud–Gharbia, et al., "Polycyclic Aryl– and Heteroarylpiperazinyl Imides as 5–HT1A Receptor Ligands and Potential Anxiolytic Agents: Synthesis and Structure–Activity Relationship Studies," *J. Med. Chem.,* 1988, 31:1382–1392.

Donald S. Robinson, et al., "Clinical Effects of the 5–HT1A Partial Agonists in Depression: A Composite Analysis of Buspirone in the Treatment of Depression," *Journal of Clinical Psychopharmacology,* 1990, 10:67S–76S.

Pierre Blier, et al., "Selective Activation of Postsynaptic 5–HT1A Receptors Induces Rapid Antidepressant Response," *Neuropsychopharmacology,* 1997, 16:333–338.

* cited by examiner

*Primary Examiner*—Jose G. Dees
*Assistant Examiner*—Michael A. Williamson
(74) *Attorney, Agent, or Firm*—Richard P. Ryan

(57) ABSTRACT

An improved method of treatment for anxiety and/or depression provides a quicker and more robust anxiolytic/antidepressant activity to a patient suffering from depression. The method comprises the concurrent administration of effective doses of certain azapirones, such as buspirone, given in a manner that suppresses formation of the 1-(2-pyrimidinyl)piperazine metabolite; and a 5-HT1A autosomal receptor antagonist, such as pindolol.

16 Claims, No Drawings

METHOD FOR TREATMENT OF ANXIETY AND DEPRESSION

CROSS REFERENCE TO RELATED APPLICATION

This application claims priority from provisional application U.S. serial No. 60/091,993 filed Jul. 7, 1998.

BACKGROUND OF THE INVENTION

The present invention relates to an improved method for treating anxious and/or depressed patients. Concurrent administration of certain azapirones with a 5-HT1A autosomal receptor antagonist provides faster onset of anxiolytic and antidepressant actions. By administering the azapirone in such a manner that formation of the 1-(2-pyrimidinyl) piperazine metabolite (1-PP) is minimized, a more robust therapeutic effect is achieved.

Certain azapirqne compounds and their pharmaceutically acceptable salts have been described as being useful in treating anxiety and depression disorders. These compounds have general structure (I) and are identified below.

| Compound | Z | Reference |
|---|---|---|
| buspirone | | U.S. Pat. No. 3,717,634 |
| gepirone | | U.S. Pat. No. 4,423,049 |
| ipsapirone | | EP 129,128 |
| tandospirone | | U.S. Pat. No. 4,507,303 |
| zalospirone | | J. Med. Chem., 1988, 31:1382–1392 |

These particular azapirones containing the pyrimidinylpiperazine moiety as an integral part of their molecular structure give rise to 1-(2-pyrimidinyl)piperazine (1-PP) as their major metabolite. This metabolite is seen in greatest abundance following oral administration. The most studied and well-known member of this compound class is buspirone, an important antianxiety agent first approved for use in anxious patients in 1986. Although buspirone has been disclosed as having antidepressant properties by Robinson, et al., *J. Clin. Psychopharmacol.*, 1990, 10:675–765; it has not been generally considered to be as efficacious as classical antidepressant agents.

However, Blier, et al. in *Neuropsychopharmacol.*, 1997, 16:333–338; reported that buspirone exhibited both an efficacy and onset of action that was superior to classical antidepressants when the buspirone was combined with the 5-HT1A autosomal receptor blocker, pindolol. Both agents were administered separately by the oral route to a group of depressed patients in the study described by Blier.

SUMMARY OF THE INVENTION

The invention concerns an improved method for treating anxiety and/or depression. The method involves concomitant administration of an azapirone, such as buspirone, gepirone, ipsapirone, tandospirone or zalospirone, and a 5-HT1A autosomal receptor antagonist such as pindolol. An improvement in rapidity of onset and efficacy of this combination of agents is provided by administration of the azapirone in a manner that suppresses formation of the major metabolite, 1-(2-pyrimidinyl)piperazine (1-PP).

DETAILED DESCRIPTION OF THE INVENTION

An objective of this invention is to provide an effective treatment for the large groups of patients suffering from anxiety, anxiety with depression symptoms, depression with anxiety symptoms and depression. These overlapping patient groups cause treatment complications with respect to differential diagnosis and appropriate pharmacological intervention. A treatment that would be applicable across these patients groups would be very beneficial, simplifying the requirement for differential diagnosis. At present, appropriate treatment of these groups requires diagnostic accuracy in order to determine whether an anxiolytic or an antidepressant agent is indicated. Buspirone, an azapirone, has been effective in treating anxiety and mixed anxiety and depression.

Experimental clinical studies regarding the role of serotonergic neuronal cell body 5-HT1A autoreceptors in delaying onset of antidepressant response have been reported. These studies also examined the role of postsynaptic 5-HT1A receptors in mediating an antidepressant response. Results of these studies have been disclosed by Blier, et al. (*Psychopharmacol. Bull.*, 1995, 31:523; *Neuropsychopharmacology*, 1997, 16:333–338). The study results provide evidence that blockade of the 5-HT1A cell body receptors by an antagonist such as pindolol, when combined with selective activation of postsynaptic 5-HT1A receptors by an agent such as buspirone may induce a faster onset and increased effectiveness of antidepressant treatment.

Pharmacologic studies have indicated that 1-PP, the major metabolite of the selected pyrimidinylpiperazinyl azapirones of this invention, can antagonize the anxiolytic and antidepressant effects seen for these compounds. The improved method of this invention utilizes methods of administration for the azapirone component of the treatment therapy that will minimize production of the 1-PP metabolite. The ratio of unchanged azapirone to 1-PP is significantly higher when the azapirone is administered either orally in an extended release formulation (NicKlasson, U.S. Pat. No. 5,431,922); transdermally; or transmucosally. Transmucosal administration involves drug delivery via the oral mucosa (buccal, sublingual absorption), nasal mucosa (transnasal absorption), vaginal and rectal mucosa.

Drug delivery formulations comprise the selected azapirones formulated into extended release oral formulations such as those described in U.S. Pat. No. 5,431,922; transdermal drug delivery devices such as skin patches, creams, ointments, and the like; oral mucosal formulations such as buccal and sublingual dosage forms (e.g. lozenges, patches, fast-dissolving tablets, chewing gum, and the like); transnasal formulations such as aerosol sprays, nose drops and nasal ointments; vaginal and rectal formulations such as suppositories, creams, ointments and the like.

Preferred routes of administration for the azapirone or an azapirone-5-HT1A antagonist combination are transdermal and transmucosal. The most preferred route is transdermal. Transdermal drug delivery devices suitable for delivery of the azapirone or a combination of the azapirone and an autosomal receptor antagonist are described in U.S. Pat. No. 5,633,009 to Kenealy, et al. and comprise devices in liquid form with a fill and seal laminate structure, peripheral adhesion laminate structures and solid state adhesive laminate structures or with the drug in the adhesive.

The 5-HT1A autosomal receptor antagonist is selected from agents such as alprenolol, WAY100135, WAY100635, (S)-UH-301, spiperone, pindolol, penbutalol, propranolol, nadolol, tetratalol, and related compounds. Pindolol is a preferred agent.

It is believed that the autosomal receptor blocker prevents an azapirone -cell body receptor interaction that shuts down firing of the serotonergic neuron. In the absence of such blockade, an azapirone, such as buspirone, causes the neuron to cease firing thereby reducing overall serotonergic transmission. Serotonergic firing rates slowly return to normal over about a two-week period in which up-regulation of receptor sites occurs. This increase in serotonergic transmission, coupled with post-synaptic agonism of the azapirone, correlates with an antidepressant effect typically seen about two weeks after beginning antidepressant medication.

The concurrent administration of an autosomal receptor antagonist, such as pindolol, and an azapirone, such as buspirone, administered in such a manner that 1-PP formation is suppressed, results in advantages for anxious and/or depressed patients. The increased ratio of the azapirone to 1-PP plasma concentrations should strengthen the anxiolytic and antidepressant efficacy. Reduction of 1-PP levels also results in reduced incidence and severity of side-effects experienced following azapirone administration. Blockade of the cell body receptor prevents the azapirone-triggered turn-off of cell firing. This results in rapid onset of the more robust antidepressant activity. Initial clinical observations indicate good patient tolerability on the buspirone-pindolol regimen.

An increase in the buspirone to 1-PP ratio appears to be desirable from a therapeutic viewpoint. The results of pharmacologic studies in laboratory animals indicate that the metabolite, 1-PP, can antagonize beneficial effects of buspirone. In rat behavioral models of anxiety, such as social intersection paradigms, and depression, such as forced-swim testing, the anxiolytic or antidepressant effect of buspirone was demonstrated to be antagonized by co-administered 1-PP.

In studies of depression, for example, buspirone was tested systemically and intracerebrally in a rat forced-swim test which is a useful screening procedure for antidepressant agents. Buspirone was active when given intracerebrally, but inactive when given systemically (where large amounts of 1-PP result). The activity of intracerebral buspirone could be blocked by systemic administration of 1-PP, thereby demonstrating its antagonism of buspirone's antidepressant effect. Other pharmacologic studies have indicated that 1-PP can antagonize beneficial effects of buspirone. Social interaction paradigms measuring levels of anxiety in rats have shown that 1-PP has an anxiogenic effect when administered to diazepam-withdrawn animals. Azapirone anxiolytics, such as buspirone, have failed to adequately relieve anxiety in patients undergoing diazepam-withdrawal, a common condition in populations of anxious patients. On the basis of these and other studies, the present improved method of buspirone administration which more reproducibly increases the ratio of unchanged buspirone to 1-PP would be expected to enhance the desired anxiolytic and antidepressant effects of buspirone. Thus, the improved method of the instant invention produces a non-obvious therapeutic advantage over previous methods of orally administering conventional formulations of buspirone.

In regard to single agent or combined agent formulations of the azapirone, e.g. buspirone, and the antagonist, e.g. pindolol, to be employed in the improved method, considerable variation in formulations and components may be practiced without departing from the instant invention. Any salt form of azapirone and antagonist having acceptable properties compatible with the selected formulation can be used. For instance: acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, (embonate), pantothenate, phosphate/diphosphate, polygalacturonate, salicylate, stearate, subacetate, succinate, sulphate, tannate, tartrate, teoclate, triethiodide. Hydrates and other pharmaceutically acceptable solvates are also included. Since the preferred routes of administration are transdermal and transmucosal, the base forms of both antagonist and azapirone will be preferred for most formulations of the present invention.

The present invention then comprises the concurrent administration of a therapeutically effective amount of an azapirone such as buspirone and a 5-HT1A autosomal receptor antagonist such as pindolol to patients suffering from anxiety and/or depression. The azapirone component of the drug regimen is administered in such a manner that the blood levels of 1-PP, the major metabolite, are minimized. Such a treatment provides an enhanced efficacy by increasing and prolonging the presence of azapirone in the patient's blood while reducing the negative therapeutic effects of the azapirone's major metabolite 1-PP by decreasing its levels in the patient's blood.

By "therapeutically effective amount" is meant an amount of azapirone or one of its salts that, when administered alone or in combination formulation, is effective to treat clinical depression. For the antagonist this means an amount that effectively blocks the neuronal 5-HT1A autoreceptor.

By "concurrent administration," "administered in combination," or the like, when referring to the antagonist component and the a2apirone component of the present method, it is meant that the components are administered concurrently to a mammal being treated. By concurrently, it is meant that each component may be administered at the same time or sequentially in any order at different points in time; however, if not administered at the same time, they should be administered in such a fashion as to provide the desired treatment effect resulting from effective simultaneous blood levels of both components. Suitable dosing intervals and dosing order with such compounds will be readily apparent to those skilled in the art, once armed with the present disclosure. Preferably, all components would be administered at the same time.

In a composition of the invention, the azapirone and antagonist, e.g. pindolol and buspirone are combined and given at various dose ratios based on the weight of azapirone deemed therapeutic for the patient and the weight of 5-HT1A antagonist sufficient to provide the desired blockade of the 5-HT1A autoreceptor.

As a general example, the azapirone such as buspirone would be administered at levels in accordance with guidelines found in standard medical/drug references such as the "Physicians Desk Reference" and the like. Generally, these levels would be equivalent in range to those provided by the oral regimen of 2.5 to 10 mg per dose for buspirone with 2 to 3 doses given per day. Amounts of pindolol for concurrent administration would generally be given to be equivalent to an oral regimen of 2.5 mg TID.

The present invention also includes pharmaceutical compositions (that is, combination products), such pharmaceutical compositions comprising or consisting essentially of, in combination, the azapirone component and the 5-HT1A antagonist component. Such compositions may be e.g. solid or liquid dosage units, transdermal patch and transmucosal formulations, and may further include other constituents such as a suitable pharmaceutical carrier, a penetration enhancer, a solubilizer for the azapirone, a stabilizer, and the like. The selection and use of these components would be known to one of skill in the area of transdermal drug delivery.

The present invention also includes pharmaceutical kits comprising or consisting essentially of the azapirone or one of its salts together with the 5-HT1A antagonist. In the kit, the azapirone component and the 5-HT1A antagonist component may each be presented in separate vials as compounds in combination with a pharmaceutically acceptable carrier. Alternatively, the azapirone component and the antagonist component may be combined together in one or more vials, with a carrier. Thus, for example, the invention includes pharmaceutical kits comprising a separate vial comprising the azapirone formulation and a separate vial comprising the 5-HT1A antagonist formulation.

The formulations and kits of the present invention may be employed in the treatment of anxiety, anxiety with depression symptoms, depression with anxiety symptoms and depression.

The preparation of both the azapirone and the 5-HT1A antagonist can be found in the literature. Specifically, buspirone, its preparation, and certain formulations are described in U.S. Pat. No. 3,717,634. Other synthetic processes for buspirone have been disclosed and buspirone itself as well as pindolol are available commercially from bulk drug manufacturers. The buspirone extended-release formulation patent (U.S. Pat. No. 5,431,922); the buspirone transdermal patch patent (U.S. Pat. No. 5,633,009), and other azapirone U.S. patents are incorporated herein in their entirety.

Dosage and Formulation

The azapirone component and 5-HT1A antagonist component combination treatment of the invention can be administered orally (in an extended-release formulation), transdermally or transmucosally by any conventional means available for the use in conjunction with pharmaceuticals, either as individual separate dosage units administered separately but concurrently, or in a physical combination of each component therapeutic agent in a single or combined dosage unit. The active agents are generally administered with a pharmaceutical carrier selected on the basis of standard pharmaceutical practice.

The dosage administered will, of course, vary depending on the use and known factors such as the age, health, and weight of the recipient; nature and extent of symptoms, kind of concurrent treatment, frequency of treatment, and the effect desired. The recipient may be any type of mammal, but is preferably a human.

In specific methods of the present invention, the two compounds, buspirone and pindolol can form the active ingredient mixture, and be typically administered in admixture with suitable pharmaceutical diluents, excipients, or carriers (collectively referred to herein as carrier materials) suitably selected with respect to the intended form of administration, that is, oral tablets or capsules for extended release oral formulations; transdermal patches, oral mucosal, nasal mucosal, rectal and vaginal mucosal formulations consistent with conventional pharmaceutical practices.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

The proper dosage of the azapirone component and the 5-HT1A antagonist component in this invention will be readily ascertainable by a medical practitioner skilled in the art, based upon clinical literature and the present disclosure.

As an example for general guidance; typically, a daily dosage would be equivalent in blood level concentrations to those provided by oral doses of about 2.5 to 10 mg of buspirone given BID or TID and about 2.5 mg pindolol given TID.

For the most preferred dosage formulation, a transdermal delivery system, the amount of each drug will vary depending on the desired dosage, permeability and thickness of the pressure-sensitive adhesive component, the skin contact time and other factors known to those skilled in the art. For buspirone, the transdermal flux should range between about 0.5 and 2.5 mg per hour. During a 24-hour period, approximately 12 to 60 mg of buspirone would be delivered.

Pharmaceutical kits useful for the treatment of anxiety and depression, which comprise a therapeutically effective amount of the buspirone component in a formulation and the antagonist formulation component, in one or more containers, are also within the ambit of the present invention. The azapirone component and the antagonist component may be in the same container or in separate containers. The containers of materials may comprise separate containers, or one or more multi-part containers, as desired. The azapirone component and the 5-HT1A antagonist component may be separate or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Various modifications of the invention in addition to those shown and described herein will be apparent to those skilled in the art from the foregoing description. Such modifications are also intended to fall within the scope of the appended claims.

What is claimed is:

1. An improved method for treating clinical anxiety and/or depression wherein the improvement comprises concurrent administration to an anxious and/or depressed patient of
    (a) an azapirone or its pharmaceutically acceptable salt selected from the group consisting of buspirone, gepirone, ipsapirone, tandospirone and zalospirone; with the azapirone being administered in such a manner as to suppress formation of the 1-pyrimidinylpiperazine metabolite, the route of administration selected from transmucosal, transdermal, or peroral using an extended release oral formulation; and
    (b) a 5-HT1A autosomal receptor antagonist or a pharmaceutically acceptable salt thereof;
        resulting in a more rapid onset of action with increased efficacy.

2. The method of claim 1 wherein the azapirone is buspirone.

3. The method of claim 2 wherein buspirone is administered transdermally.

4. The method of claim 1 wherein the 5-HT1A antagonist is selected from alprenolol, WAY100135, WAY100635, (S)-UH-301, spiperone, pindolol, penbutalol, propranolol, nadolol, tetratalol, and related compounds.

5. The method of claim 4 wherein the 5-HT1A antagonist is pindolol.

6. The method of claim 1 wherein the azapirone and 5-HT1A antagonist are administered in combination.

7. The method of claim 6 wherein the combination of azapirone and 5-HT1A antagonist are administered by a transdermal patch.

8. The method of claim 7 wherein the azapirone is buspirone and the 5-HT1A antagonist is pindolol.

9. A pharmaceutical composition comprising a therapeutically effective amount of an azapirone, or a pharmaceutically acceptable salt or hydrate thereof, and a 5-HT1A autosomal receptor antagonist.

10. A pharmaceutical composition of claim 7 wherein the azapirone is buspirone and the 5-HT1A antagonist is pindolol.

11. A pharmaceutical kit comprising (1) a transmucosal, transdermal, or extended release oral dosage form of buspirone and (2) a dosage formulation of a 5-HT1A autosomal receptor antagonist, or a pharmaceutically acceptable salt thereof.

12. The pharmaceutical kit of claim 9 wherein the azapirone is buspirone and the 5-HT1A antagonist is pindolol.

13. A transdermal drug delivery device comprising an azapirone and a 5-HT1A antagonist.

14. The transdermal device of claim 13 wherein the azapirone is buspirone.

15. The transdermal device of claim 13 wherein the 5-HT1A antagonist is pindolol.

16. A transdermal drug delivery device comprising:
    (a) a pressure-sensitive adhesive layer containing buspirone, pindolol, and a solubilizing agent, the pressure-sensitive adhesive layer having a first face and a second face, and
    (b) a backing layer substantially impermeable to the buspirone and pindolol, and contacting the first face of the pressure-sensitive adhesive layer.

* * * * *